US011045358B2

United States Patent
Hartwell et al.

(10) Patent No.: US 11,045,358 B2
(45) Date of Patent: *Jun. 29, 2021

(54) BESPOKE WOUND TREATMENT APPARATUSES AND METHODS FOR USE IN NEGATIVE PRESSURE WOUND THERAPY

(71) Applicant: Smith & Nephew PLC, Watford (GB)

(72) Inventors: Edward Yerbury Hartwell, Hull (GB); Mark Richardson, Grimsby (GB); Carl Saxby, Brough (GB)

(73) Assignee: Smith & Nephew PLC, Watford (GB)

( * ) Notice: Subject to any disclaimer, the term of this patent is extended or adjusted under 35 U.S.C. 154(b) by 169 days.

This patent is subject to a terminal disclaimer.

(21) Appl. No.: 16/222,055

(22) Filed: Dec. 17, 2018

(65) Prior Publication Data

US 2019/0254878 A1 Aug. 22, 2019

Related U.S. Application Data

(63) Continuation of application No. 14/420,134, filed as application No. PCT/IB2013/002494 on Aug. 8, 2013, now Pat. No. 10,154,928.

(Continued)

(51) Int. Cl.
*A61M 35/00* (2006.01)
*A61M 1/00* (2006.01)
*A61F 13/00* (2006.01)
*A61B 5/00* (2006.01)
*A61B 5/107* (2006.01)
(Continued)

(52) U.S. Cl.
CPC ...... *A61F 13/00021* (2013.01); *A61B 5/0064* (2013.01); *A61B 5/1079* (2013.01); *A61F 13/00051* (2013.01); *A61F 13/00987* (2013.01); *A61M 1/0088* (2013.01); *A61M 31/00* (2013.01)

(58) Field of Classification Search
CPC .......... A61M 35/00; A61M 1/00; A61M 3/00; A61M 31/00; A61F 13/00; A61F 13/02; A61F 8/44
See application file for complete search history.

(56) References Cited

U.S. PATENT DOCUMENTS 5,636,643 A 6/1997 Argenta et al.
7,754,937 B2 7/2010 Boehringer et al.
(Continued)

FOREIGN PATENT DOCUMENTS

CN 1453749 11/2003
EP 2 366 721 9/2011
(Continued)

OTHER PUBLICATIONS

U.S. Appl. No. 61/929,864, filed Jan. 21, 2014, Hartwell et al.
(Continued)

*Primary Examiner* — Tatyana Zalukaeva
*Assistant Examiner* — Ilya Y Treyger
(74) *Attorney, Agent, or Firm* — Knobbe, Martens, Olson & Bear, LLP

(57) ABSTRACT

Methods and apparatuses are disclosed relating to the creation and use of bespoke wound fillers and other wound treatment apparatuses. Some embodiments provide for the creation of bespoke wound fillers based on characteristics of a wound. Certain embodiments also include the use of bespoke wound fillers in combination with negative pressure to treat a wound.

15 Claims, 9 Drawing Sheets

Related U.S. Application Data

(60) Provisional application No. 61/681,093, filed on Aug. 8, 2012.

(51) Int. Cl.
*A61M 3/00* (2006.01)
*A61M 31/00* (2006.01)

(56) References Cited

U.S. PATENT DOCUMENTS

| | | | |
|---|---|---|---|
| 7,799,004 B2 | 9/2010 | Tumey | |
| 7,910,789 B2 | 3/2011 | Sinyagin | |
| 8,535,296 B2 | 9/2013 | Blott et al. | |
| 8,588,893 B2 | 11/2013 | Jaeb et al. | |
| 8,764,732 B2 | 7/2014 | Hartwell | |
| 8,791,316 B2 | 7/2014 | Greener | |
| 9,301,880 B2 | 4/2016 | Lina et al. | |
| 10,154,928 B2 | 12/2018 | Hartwell et al. | |
| 2007/0185463 A1 | 8/2007 | Mulligan | |
| 2008/0316209 A1 | 12/2008 | Wen | |
| 2009/0204423 A1 | 8/2009 | DeGheest et al. | |
| 2009/0326429 A1 | 12/2009 | Siniaguine | |
| 2010/0191196 A1 | 7/2010 | Heagle | |
| 2010/0241447 A1 | 9/2010 | Siniaguine et al. | |
| 2012/0321878 A1 | 12/2012 | Landon et al. | |
| 2013/0211349 A1 | 8/2013 | Stokes et al. | |
| 2013/0310781 A1 | 11/2013 | Phillips et al. | |
| 2013/0338437 A1 | 12/2013 | Abuzaina | |
| 2014/0088402 A1 | 3/2014 | Xu | |
| 2014/0228786 A1 | 8/2014 | Croizat et al. | |
| 2014/0249493 A1 | 9/2014 | Hartwell | |
| 2014/0350496 A1 | 11/2014 | Riesinger | |
| 2015/0159066 A1 | 6/2015 | Hartwell et al. | |
| 2016/0346444 A1 | 12/2016 | Zamierowski | |
| 2017/0007462 A1 | 1/2017 | Hartwell et al. | |
| 2017/0136700 A1 | 5/2017 | Li et al. | |
| 2017/0348153 A1 | 12/2017 | Robinson et al. | |

FOREIGN PATENT DOCUMENTS

| | | |
|---|---|---|
| EP | 2 529 767 | 12/2012 |
| EP | 2 684 526 | 1/2014 |
| EP | 2 694 526 | 2/2014 |
| EP | 2694526 A2 | 2/2014 |
| JP | 2011-505871 | 3/2011 |
| JP | 2011-513003 | 4/2011 |
| JP | 2012-513825 | 6/2012 |
| RU | 2435520 | 12/2011 |
| WO | WO 2003/094811 | 11/2003 |
| WO | WO 2005/091884 | 10/2005 |
| WO | WO 2009/016605 | 2/2009 |
| WO | WO 2009/071928 | 6/2009 |
| WO | WO 2009/149250 | 12/2009 |
| WO | WO 2010/059612 | 5/2010 |
| WO | WO 2010/092334 | 8/2010 |
| WO | WO 2012/069793 | 5/2012 |
| WO | WO 2012/069794 | 5/2012 |
| WO | WO 2013/076450 | 5/2013 |
| WO | WO 2013/136181 | 9/2013 |
| WO | WO 2014/024048 | 2/2014 |
| WO | WO 2015/116823 | 8/2015 |

OTHER PUBLICATIONS

"3D Printer", American Heritage Dictionary of the English Language, Fifth Edition, 2016, accessed Feb. 22, 2018, in 1 page. URL: https://www.thefreedictionary.com/3D+printer.

International Search Report, re PCT Application No. PCT/IB2013/002494, dated Jan. 28, 2014.

International Preliminary Report on Patentability, re PCT Application No. PCT/IB2013/002494, dated Feb. 19, 2015.

International Search Report and Written Opinion, re PCT Application No. PCT/EP2015/050959, dated May 8, 2015.

BESPOKE WOUND TREATMENT APPARATUSES AND METHODS FOR USE IN NEGATIVE PRESSURE WOUND THERAPY

CROSS-REFERENCE TO RELATED APPLICATIONS

This application is a continuation application of U.S. application Ser. No. 14/420,134, filed Feb. 6, 2015, which is a U.S. National Phase of PCT International Application No. PCT/IB2013/002494, filed Aug. 8, 2013 entitled BESPOKE WOUND TREATMENT APPARATUSES AND METHODS FOR USE IN NEGATIVE PRESSURE WOUND THERAPY, which claims the benefit of U.S. Provisional Application No. 61/681,093, filed Aug. 8, 2012 entitled BESPOKE WOUND FILLER DEVICES. The contents of the aforementioned applications are hereby incorporated by reference in their entireties as if fully set forth herein. The benefit of priority to the foregoing applications is claimed under the appropriate legal basis, including, without limitation, under 35 U.S.C. § 119(e).

BACKGROUND OF THE INVENTION

Field of the Invention

Embodiments described herein relate to wound fillers, in particular wound fillers for use with negative pressure wound therapy, and that may be fabricated or created in a bespoke or custom manner for use in wound treatment.

Description of the Related Art

Wound fillers, especially for use in negative pressure therapy, play a critical role in wound treatment. Nevertheless, sizing wound fillers for use in a wound can be difficult, time consuming, and imperfect, especially for irregularly-shaped wounds.

SUMMARY OF THE INVENTION

Accordingly, embodiments described herein relate to devices, methods, and systems for providing bespoke or customized wound fillers for the treatment of a wound. In certain embodiments, a bespoke wound filler is fabricated and optimized for use with negative pressure wound therapy. Preferably, a bespoke wound filler may be created by obtaining a three-dimensional scan or model of a wound, and manufacturing a bespoke wound filler configured to be used with the wound.

In certain embodiments, a method of manufacturing a wound filler for use in negative pressure wound therapy comprises: scanning a wound to obtain a three-dimensional model of a wound space to be treated with negative pressure wound therapy; modifying the three-dimensional model of the wound space to generate a three-dimensional model of a wound filler, wherein said modifying accounts for attributes of the wound and for a negative pressure wound therapy treatment modality; and fabricating a wound filler based on the generated three-dimensional model of the wound filler.

In some embodiments, the three-dimensional model of the wound space is obtained using a device selected from the group consisting of laser scanners, stereo-optical scanners, and cameras with depth sensors. In certain embodiments, the three-dimensional model of the wound filler is generated using a repeating building block. In further embodiments, the three-dimensional model of the wound filler comprises repeating blocks having different characteristics for positioning in different parts of the wound space.

In certain embodiments involving the aforementioned method of manufacturing a wound filler for use in negative pressure wound therapy, modification of the three-dimensional model of the wound space accounts for one or more tissue types present in the wound volume. Some embodiments provide for a wound filler that is fabricated with a three-dimensional printer. In some embodiments, generating the three-dimensional model of the wound filler comprises determining a suitable porosity for the wound filler. In further embodiments, the three-dimensional model of the wound filler has variable porosity.

In some embodiments, fabricating the wound filler comprises fabricating a first wound contacting portion of the wound filler using a first porosity, and fabricating a second portion of the wound filler using a second porosity, the first porosity being smaller than the second porosity. In further embodiments, the wound filler is fabricated from a polymer. In some embodiments, the wound filler is fabricated from a porous scaffolding material.

In certain embodiments, fabricating the wound filler further comprises seeding the wound filler with one or more of cells or cell growth promoters. In further embodiments, the wound filler is fabricated from two or more different materials.

In another embodiment, an apparatus for treating a wound with negative pressure therapy is provided, comprising a bespoke wound filler having a controlled porosity adapted to treat the wound with negative pressure wound therapy and having a shape and configuration constructed to custom fit into the wound. In certain embodiments, the apparatus further comprises a drape configured to be placed over the bespoke wound filler and to be sealed to skin surrounding the wound. In other embodiments, the apparatus further comprises a port configured to connect the drape to a source of negative pressure. In further embodiments, the apparatus comprises a source of negative pressure configured to apply negative pressure to the wound filler under the drape.

In some embodiments, the bespoke wound filler comprises repeating building blocks. In further embodiments, the bespoke wound filler comprises repeating building blocks having different characteristics for positioning in different parts of the wound. Some embodiments provide for the bespoke wound filler to have a varying porosity. In further embodiments, the bespoke wound filler comprises a material with smaller pores which encapsulates or is placed underneath a material with larger pores. In some embodiments, the smaller pores measure between 20 to 150 µm, and the larger pores measure between 400-3000 µm. In further embodiments, the bespoke wound filler has a porosity configured for contact with two or more different tissue types, and wherein the porosity of the filler configured to contact the two or more different tissue types is different.

Some embodiments provide for a method of treating a wound with negative pressure wound therapy using any of the apparatuses described herein in this section or any other section of this specification, comprising placing the bespoke wound filler into the wound and treating the wound with negative pressure wound therapy.

Some embodiments provide for a bespoke wound filler that is manufactured by scanning the wound to obtain a three-dimensional model of a wound space to be treated with negative pressure; modifying the three-dimensional model to account for attributes of the wound and for a negative pressure wound therapy treatment modality; and fabricating the bespoke wound filler based on the modified three-dimensional model.

In any of the embodiments of the apparatuses and/or methods described herein, a bespoke wound treatment apparatus may comprise constructing not only a bespoke wound filler, but also constructing other components of the wound treatment apparatus. In some embodiments, the apparatuses and methods described herein may be utilized to construct an entire or portion of a wound dressing which may comprise multiple layers, such as a wound contact layer, absorbent layer, wound cover, overlay or drape, a port, a conduit, a fluidic connector and a negative pressure source. In some embodiments, a combination of the components of a wound dressing (e.g., a wound filler and a wound overlay) may be made in a customized manner wherein the combined structure is manufactured as a single entity according to the methods described herein.

In any of the embodiments of the apparatuses and/or methods described herein, a bespoke wound treatment apparatus may comprise components configured to irrigate a wound. In certain embodiments of the methods described herein, a bespoke wound filler placed in a wound is later replaced by a different bespoke wound filler after an interval of time has passed.

BRIEF DESCRIPTION OF THE DRAWINGS

Other features and advantages of the present invention will be apparent from the following detailed description of the invention, taken in conjunction with the accompanying drawings of which.

DETAILED DESCRIPTION OF THE PREFERRED EMBODIMENTS

Figure 1:
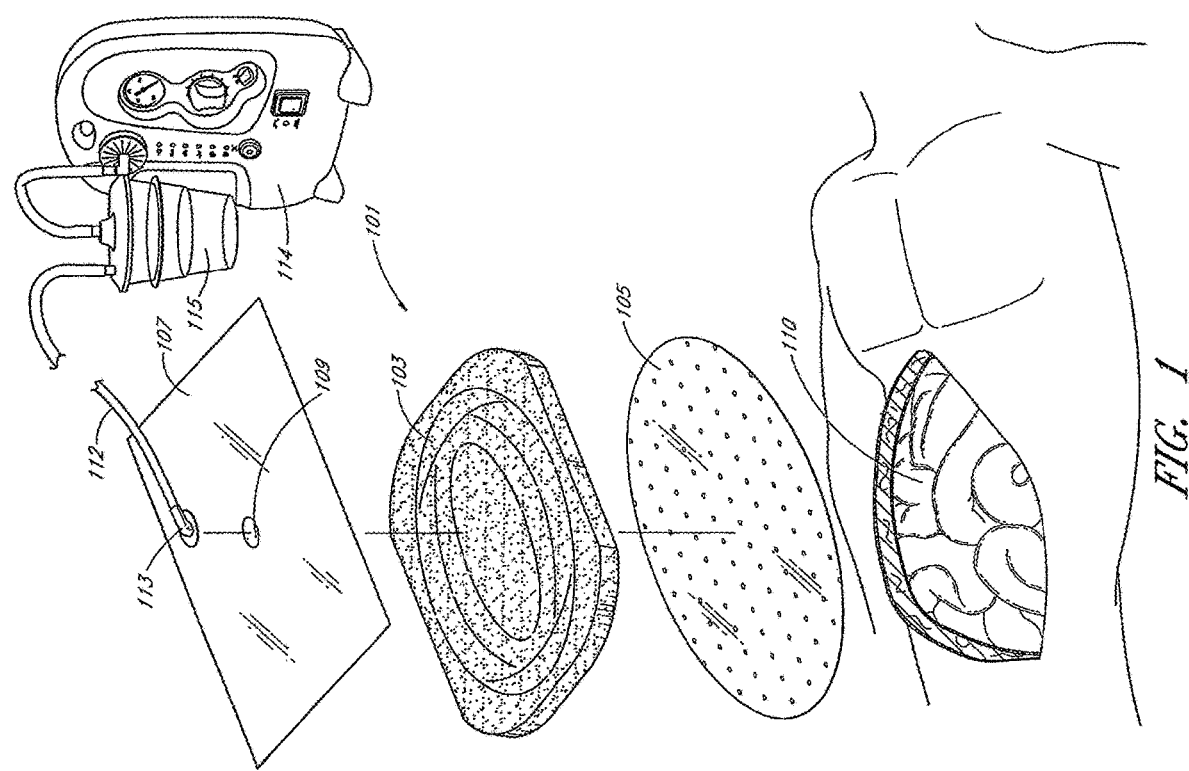
FIG. 1 is a schematic illustration of a negative pressure system.

Embodiments disclosed herein relate to apparatuses and methods of treating a wound, especially with reduced pressure. Embodiments for use with negative pressure include pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

As is used herein, reduced or negative pressure levels, such as $-X$ mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of $-X$ mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., $-40$ mmHg is less than $-60$ mmHg). Negative pressure that is "more" or "greater" than $-X$ mmHg corresponds to pressure that is further from atmospheric pressure (e.g., $-80$ mmHg is more than $-60$ mmHg).

The negative pressure range for some embodiments of the present disclosure can be approximately $-80$ mmHg, or between about $-20$ mmHg and $-200$ mmHg. Note that these pressures are relative to normal ambient atmospheric pressure. Thus, $-200$ mmHg would be about 560 mmHg in practical terms. In some embodiments, the pressure range can be between about $-40$ mmHg and $-150$ mmHg. Alternatively a pressure range of up to $-75$ mmHg, up to $-80$ mmHg or over $-80$ mmHg can be used. Also in other embodiments a pressure range of below $-75$ mmHg can be used. Alternatively, a pressure range of over approximately $-100$ mmHg, or even 150 mmHg, can be supplied by the negative pressure apparatus. In some embodiments, the negative pressure range can be as small as about $-20$ mmHg or about $-25$ mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include application Ser. No. 11/919,355, titled "WOUND TREATMENT APPARATUS AND METHOD," filed Oct. 26, 2007, published as US 2009/0306609; and U.S. Pat. No. 7,753,894, titled "WOUND CLEANSING APPARATUS WITH STRESS," issued Jul. 13, 2010. Both applications are hereby incorporated by reference in their entirety.

Turning to FIG. 1, treatment of a wound with negative pressure in certain embodiments uses a negative pressure treatment system 101 as illustrated schematically here. In this embodiment, a wound site 110, illustrated here as an abdominal wound site, may benefit from treatment with negative pressure. However, many different types of wounds may be treated by such a method, and the abdominal wound illustrated here is merely one particular example. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive responses to treatment by the application of negative pressure include infected open wounds, decubitus ulcers, dehisced incisions, partial thickness burns, and various lesions to which flaps or grafts have been attached. Consequently, the application of negative pressure to a wound site 110 can be beneficial to a patient.

Accordingly, certain embodiments provide for a wound contact layer 105 to be placed over the wound site 110. Preferably, the wound contact layer 105 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound site 110 or the transmittal of negative pressure to the wound site 110. Additional embodiments of the wound contact layer 105 are described in further detail below.

Certain embodiments of the negative pressure treatment system 101 may also use a wound filler 103, which may be a bespoke wound filler as will be described in much greater detail below and which can be disposed over the wound contact layer 105 or into direct contact with the wound. The wound filler 103 shown in FIG. 1 is merely illustrative of one configuration of a wound filler that may be utilized, wherein portions of the wound filler may be torn away to appropriately size the wound filler. In some embodiments, the bespoke wound fillers described in greater detail below eliminate the need to provide a wound filler that needs to be cut or sized by the clinician before applying the wound filler into the wound. In certain embodiments, the wound filler of any of the embodiments described herein is applied directly to the wound with or without a wound contact layer 105 and/or a drape 107. This filler 103 can be constructed from a porous material, for example foam, that is soft, resiliently flexible, and generally conformable to the wound site 110.

Such a foam can include an open-celled and reticulated foam made, for example, of a polymer. Suitable foams include foams composed of, for example, polyurethane, silicone, and polyvinyl alcohol. In certain embodiments, this filler 103 can channel wound exudate and other fluids through itself when negative pressure is applied to the wound. Some fillers 103 may include preformed channels or openings for such purposes. Other embodiments of wound fillers that may be used in place of or in addition to the filler 103 are discussed in further detail below.

In some embodiments, a drape 107 is used to seal the wound site 110. The drape 107 can be at least partially liquid impermeable, such that at least a partial negative pressure may be maintained at the wound site. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling of the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. application Ser. No. 10/533,275, filed Oct. 28, 2003, titled "APPARATUS FOR ASPIRATING, IRRIGATING, AND CLEANSING WOUNDS," issued as U.S. Pat. No. 7,524,315 discloses other similar aspects of negative pressure systems and is hereby incorporated by reference in its entirety. All references in this application that are incorporated in their entireties should be considered as if fully set forth herein.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or oleophobic filter in the container to prevent overflow; other embodiments may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister. In further embodiments, the aforementioned wound treatment system may be combined with a fluid source to allow for irrigation of the wound.

In other embodiments, a negative pressure wound therapy apparatus may utilize a canister-less system, such as the PICO system available from Smith & Nephew. In some embodiments, a wound dressing may be provided comprising an absorbent layer such as a superabsorbing material configured to store wound exudate therein. The absorbent layer may be contained between a wound cover or backing layer and an optional wound contact layer, and the entire dressing may include a port configured to be connected to a source of negative pressure. Such dressings may include multiple layers configured to facilitate transmission of negative pressure to a wound site and also to promote flow of fluid into the absorbent layer. Further details regarding wound treatment apparatuses and methods incorporating absorbent materials, transmission layers and other components are found in U.S. application Ser. No. 10/575,871, filed Jan. 29, 2007, titled "WOUND CLEANSING APPARATUS IN-SITU," issued as U.S. Pat. No. 7,964,766; U.S. application Ser. No. 12/744,055, filed May 20, 2010, titled "VACUUM ASSISTED WOUND DRESSING," published as US2011/0009838; U.S. application Ser. No. 12/744,277, filed Sep. 20, 2010, titled "WOUND DRESSING," published as US2011/0028918; U.S. application Ser. No. 12/744,218, filed Sep. 20, 2010, titled "WOUND DRESSING," published as US2011/0054421; U.S. application Ser. No. 13/092,042, filed Apr. 21, 2011, titled "WOUND DRESSING AND METHOD OF USE," published as US2011/0282309; U.S. application Ser. No. 11/432,855, filed May 11, 2006, titled "DEVICE AND METHOD FOR WOUND THERAPY," issued as U.S. Pat. No. 7,615,036; U.S. application Ser. No. 11/610,458, filed Dec. 13, 2006, titled "DEVICE AND METHOD FOR WOUND THERAPY," issued as U.S. Pat. No. 7,779,625; U.S. application Ser. No. 12/592,049, filed Nov. 18, 2009, titled "DEVICE AND METHOD FOR WOUND THERAPY," issued as U.S. Pat. No. 8,460,255; PCT Application No. PCT/US13/53075, filed Jul. 31, 2013, titled "WOUND DRESSING AND METHOD OF TREATMENT"; U.S. application Ser. No. 11/517,210, filed Sep. 6, 2006, titled "SELF CONTAINED WOUND DRESSING WITH MICROPUMP," issued as U.S. Pat. No. 7,569,742; U.S. application Ser. No. 11/516,925, filed Sep. 6, 2006, titled "WOUND DRESSING WITH VACUUM RESERVOIR," issued as U.S. Pat. No. 7,699,823; U.S. application Ser. No. 11/516,216, filed Sep. 6, 2006, titled "SELF-CONTAINED WOUND DRESSING APPARATUS," published as US2007/0055209; the entireties of each of which are hereby incorporated by reference.

Figure 2:
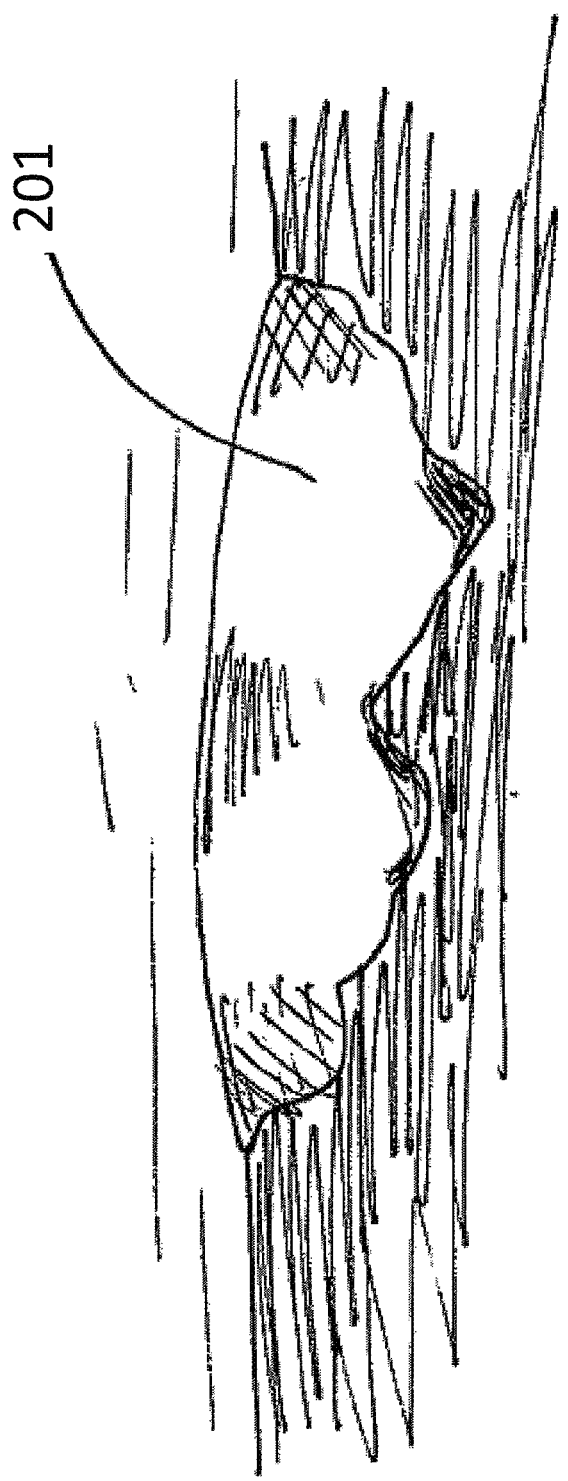
FIG. 2 is a schematic illustration of a wound with irregular margins.

FIG. 2 illustrates a wound 201 that may require filling with a bespoke wound filler so as to appropriately treat and heal the wound. Preferably, the wound 201 will be treated with negative pressure. The margins and contours of the wound 201 as illustrated are irregular, rendering it difficult to fill the wound with conventional fillers.

Figure 3:
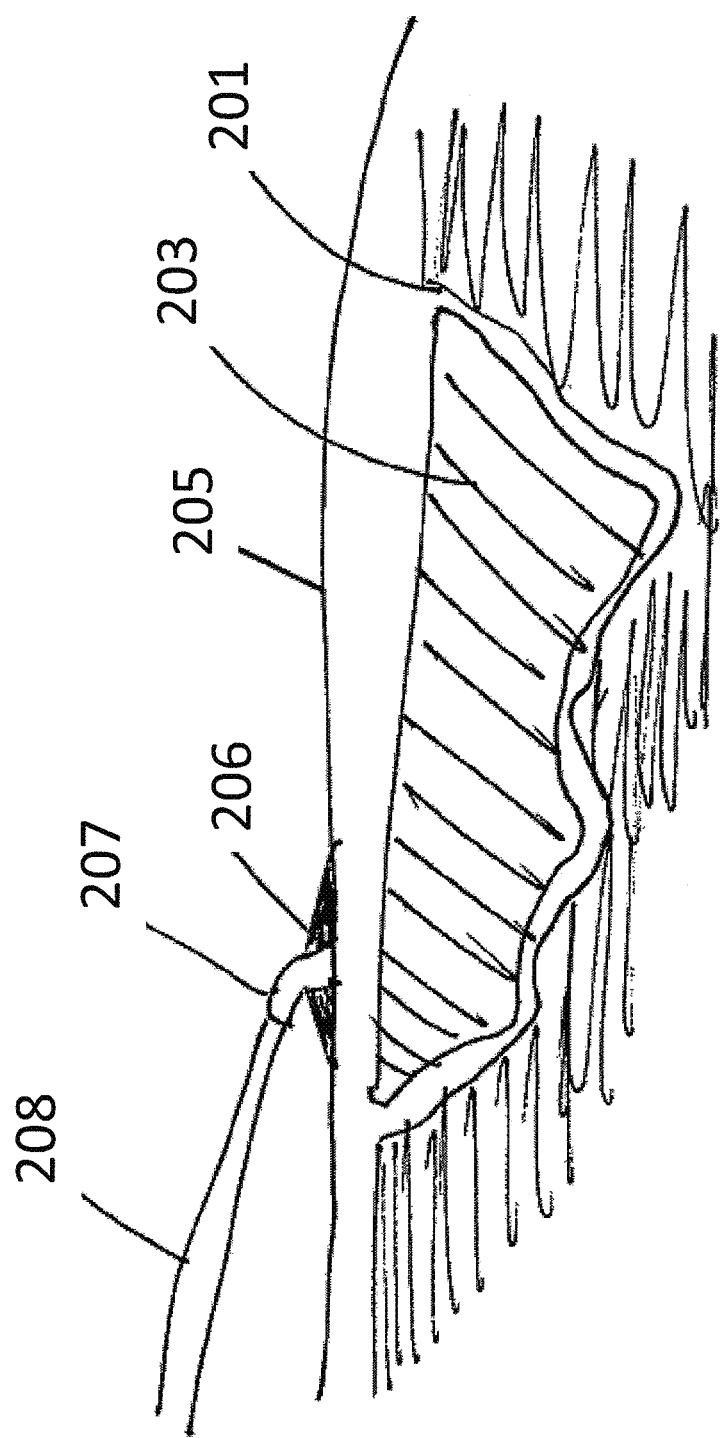
FIG. 3 is a schematic illustration of the wound from FIG. 1 filled with an embodiment of a bespoke wound filler and used in conjunction with a negative pressure treatment system.

FIG. 3 illustrates the wound 201 having a bespoke filler 203 inserted therein. Preferably, a liquid-impermeable drape 205 is placed over the wound and sealed against skin proximate the wound margins, for example with an adhesive. An aperture 206 may be made into the drape 205 so as to provide a fluidic connection to a source of negative pressure (not illustrated) such as a vacuum pump. Preferably, the aperture 206 communicates with a fluidic connector or port 207, which may be attached to the source of negative pressure via a conduit 208. Further details regarding negative pressure systems, apparatuses and methods that may be utilized with the systems, apparatuses and methods described herein are found in U.S. application Ser. No. 13/381,885, filed Dec. 30, 2011, titled "APPARATUSES AND METHODS FOR NEGATIVE PRESSURE WOUND THERAPY," published as US2012/0116334; U.S. application Ser. No. 12/886,088, filed Sep. 20, 2010, titled "SYSTEMS AND METHODS FOR USING NEGATIVE PRESSURE WOUND THERAPY TO MANAGE OPEN ABDOMINAL WOUNDS," published as US2011/0213287; U.S. application Ser. No. 13/092,042, filed Apr. 21, 2011, titled "WOUND DRESSING AND METHOD OF USE," published as US2011/0282309; the entireties of each of which are hereby incorporated by reference.

Figure 4:
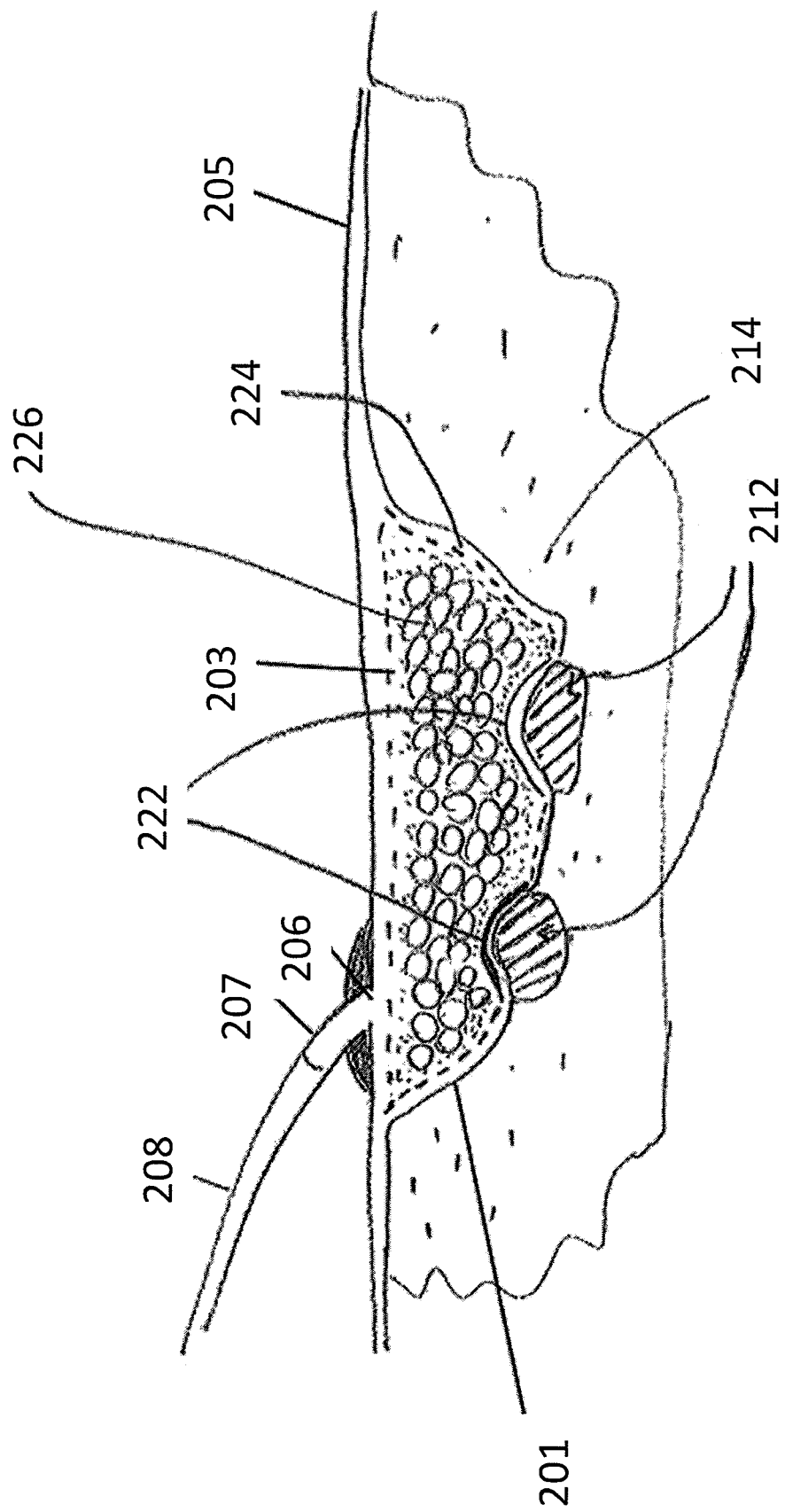
FIG. 4 is a schematic illustration of a wound comprising multiple tissue types being treated with an embodiment of a bespoke wound filler used in conjunction with a negative pressure treatment system.

FIG. 4 illustrates an example of a bespoke wound filler 203 used in conjunction with a wound 201. A drape 205 is placed over the wound 201 and sealed (e.g., using an adhesive) against the surrounding skin near the wound margins. Preferably, an aperture 206 through the drape 205 communicates with a source of negative pressure (not illustrated), and a port 207 may be used as a fluidic connector between the wound and the source of negative pressure. A conduit 208 may communicate with the source of negative pressure and the wound. Unlike FIG. 3, the wound 201 in FIG. 4 comprises different tissue anatomy, including exposed bone areas 212, in addition to soft tissue areas 214. Of course, other tissue types may be present, including for example muscles, nerves, ligaments, tendons, or any other tissue that may become exposed within a wound. According to some embodiments described herein this section and in greater detail below, the bespoke wound filler 203 is customized to the size and environment of the wound 201. The wound filler 203 illustrated here therefore comprises a first contacting area 222 configured to contact the exposed bone areas 212 and a second contacting area 224 configured to contact the soft tissue areas 214. In some embodiments, the first contacting area 222 may be occlusive, substantially fluid-impermeable, or have few to no pores, so as to limit the amount of fluid removed from and negative pressure applied to, the exposed bone area 212. In some embodiments, conversely, the second contacting area 224, when configured to contact the soft tissue areas 214, may be configured to be porous so as to enhance fluid removal and granulation tissue growth upon application of negative pressure. In some embodiments, the interior body 226 of the bespoke wound filler 203 may be of a different porosity than other areas; preferably, it comprises a material with greater porosity or larger pores than the wound-contacting surfaces. Such configurations may be preferable to enhance fluid removal, because, since the larger pores are not in contact with the wound 101, granulation tissue from the wound 101 will not grow into the larger pores.

Generally, the bespoke filler 203 may be constructed so as to provide a bespoke or custom fit into a wound 201. As will be described in greater detail below, various attributes of the bespoke filler may be modified, including its dimensions, density, material characteristics (including the use of multiple materials), physical characteristics, chemical characteristics, molecular delivery mechanisms, structural characteristics, and other attributes. In some embodiments, portions of the bespoke wound filler may have characteristics favorable to the application of negative pressure. In certain embodiments, the bespoke wound filler may have characteristics that are favorable to the application of irrigation.

Generating a 3D Scan of a Wound

The general shape and configuration of the bespoke filler 203 is preferably determined in relation to the shape and volume of the wound 201. The shape and volume of the wound 201 may be determined by any suitable method, but is preferably done by creating a three-dimensional (3D) scan of the wound 201. Although reference to 3D scans and/or 3D modeling is made herein this section and throughout the specification, 2D scanning or 2D modeling may also be used in place of the 3D scans and/or 3D models.

Preferably, a device capable of obtaining a 3D scan of the wound 201 is used that does not make contact with the wound. Such devices include laser scanners (particularly laser scanners employing triangulation techniques), stereo-optical scanners, or cameras with depth sensors such as those used in the Microsoft XBOX Kinect®. Other suitable devices include 3D Systems' ZScanner® 800. Preferably, the 3D scan device is capable of scanning a wound to an accuracy of at least about: 1 μm, 5 μm, 10 μm, 20 μm, 30 μm, 40 μm, 50 μm, 60 μm, 70 μm, 80 μm, 80 μm, or 100 μm. In some embodiments, other methods of obtaining a scan may be used such as deriving a scan from an analog or digital image of the wound.

3D scans may also be generated via CT or MRI images, for example by "stacking" multiple images together to form a 3D model. In certain embodiments, devices that contact the wound (e.g., via a pressure sensitive stylus), may also be used. In other embodiments, physical molds of the wound may be used to create a 3D scan. These physical molds may be fabricated from any suitable material such as Jeltrate or other alginate or silicone based materials often used for taking dental impressions.

In some embodiments, the tissue is stained with various markers that can be used to generate a more accurate 3D model. For example, the wound may be stained with markers that identify particular cell types that may be present at the wound site such as the various host cells of the patient or bacterial cells. Cell markers may give an improved overall understanding of the wound by indicating the different stages of healing of various areas of the wound or by providing information relating to infection. Additional markers may be used to stain extra-cellular matrix proteins, thus providing information about the surrounding structure and state of healing in the wound. Stained tissue can be imaged and analyzed via any suitable imaging technique, such as fluorescence microscopy or other techniques. However, imaging of a stained wound is not limited to microscopic techniques and may be performed via any suitable technique. Preferably, the characteristics data collected from staining the wound may be incorporated in the 3D model of the wound, matching particular stained areas to particular regions of the model.

Assorted hardware and software necessary to interpret and generate a 3D scan, and that is usually provided with the devices, is also used. Such hardware and software may preferably be configured to interface with a personal computer. Some embodiments may also provide for a miniaturized and/or self-contained 3D scanning device that comprises integrated software and/or hardware.

In some embodiments, the 3D scanning device may be configured to interface with a telephone or tablet computer. Some embodiments may also provide for a patient to generate a 3D scan themselves (e.g., by using a Kinect® sensor), sending or uploading the 3D scan or model to a service provider, and having the service provider create and send a bespoke wound filler 203 customized to the patient's particular wound.

Generation of a 3D Model of the Wound Filler

The 3D scanning device will preferably generate a 3D wound model of the volume of the wound space using appropriate software. Such a 3D wound model is then modified to include a 3D model of the appropriate wound filler. Suitable software includes Solidworks, Solid Edge, and other 3D CAD programs. In certain embodiments, such 3D data sets of the wound surface volume are generated by subtracting the data set for the wound scan away from a volume larger in overall dimensions than the wound volume dimensions. Some embodiments may provide for the generation of an inverse of the scan surface volume. the inverse of the scan surface volume may be generated. The data files generated may be in STL, STEP, IGES file formats, other 3D model file types, plain text files, or any suitable file format. The words "3D model" may be generally used throughout the specification to describe a 3D model of the wound alone, a 3D model of the filler alone, a 3D model of the wound with filler, or a 3D surface model of the wound surface. The use of any of the above-mentioned types of models is applicable to any of the embodiments described herein this section and elsewhere in the specification.

Preferably, the software program will modify and/or normalize the 3D wound model obtained from the 3D scanning device so as to make it usable in 3D printing devices (as described below). For example, the software program may modify the 3D model to make the mesh manifold, remove inverted normals, and optimize detail sizes, wall thicknesses, and orientations for use in the 3D printing device. Additionally, the software will preferably make the top of the 3D model flush with the surrounding skin, although in some embodiments, it may be preferable for the bespoke filler (and consequently, the 3D filler model) to extend above the skin at least in part.

At this stage, attributes of the 3D model may also be modified to account for various factors in the wound environment or to account for particular treatment modalities. A wound will typically contain multiple regions that may be in different stages of healing. For example, a wound may have areas that: are exudating heavily, are infected, are bleeding, contain dead/dying tissue, are drying, are inflamed, or in various other states. Further, the different areas of the wound may comprise different types of tissue, such as bone, cartilage, blood vessels, skin, fat, or any other organs or tissues. To effectively treat these variable tissue types and conditions may require different types of fillers with different physical and chemical characteristics as will be described in greater detail below.

The use of negative pressure in combination with various wound fillers has been demonstrated to effectively improve wound healing. However, such a combination is most effective when the wound filler is tailored to most effectively apply negative pressure to a particular type of wound. For example, as is described herein this section and elsewhere in the specification, a filler with a desired porosity may allow for an increased volume of fluid to be drawn from a wound at a greater rate. Additionally, as will be described in greater detail below, wound fillers may be tailored to more effectively deliver irrigant fluid to a wound.

For example, and as described in further detail below, attributes of the 3D model may be modified to account for different tissue types in the wound, such as exposed bone or tendon, and which may require that the wound filler be different from wound filler to be used in the treatment of epidermal, sub-epidermal, or muscle tissue. FIG. 4, as described above, describes such an embodiment.

In some embodiments, a human may assist in the creation of a 3D model, leading to the construction of a bespoke wound filler, by identifying the properties of the various regions of the wound. Hereinafter the word "clinician" will be used to describe any human involved in the creation of the filler, however "clinician" is not limited to only medical practitioners, but could be a home user, general caregiver, or patient.

The clinician may contribute to the creation of a 3D model for a desired wound filler by identifying the characteristics of the various regions of a wound which may be treated with the wound filler, for example while under negative pressure. For instance, a clinician may identify areas as highly exudating, drying, infected, or having any other condition described herein this section or elsewhere in the specification. A clinician may further identify the tissue type of the various regions of the 3D model. The clinician can identify and define characteristics of the wound such as the shape of the wound, severity of the wound, expected closure of the wound, or any other relevant characteristic of the wound. The clinician may further identify the fluid modality of a particular area of a wound, such as by identifying the level of fluid release from such a portion of the wound. Additionally, the clinician can further identify areas of the wound that would be best served by the application of various levels of negative pressure. Further, the clinician may identify areas that would be best served by irrigation and/or the delivery of various molecules. In addition to the characteristics already described, a clinician may identify any other key characteristics that may influence the healing and closure of a wound or impact the health of a patient.

Identification of the characteristics of a wound can be performed in a variety of ways as described herein this section and elsewhere in the specification. In some embodiments, the wound is assessed by visual inspection of the wound via computer or human recognition. In certain embodiments, the assessment of the wound is completed using chemical, physical, auditory, or energy-based assays or imaging techniques. In further embodiments, any suitable identification techniques may be used.

In further embodiments, the clinician may also assess additional health-related factors of the patient and incorporate those factors into the 3D wound model. For example, the clinician could identify a diabetic patient, and recognize that their circulation may be compromised. Thus, the wound model could be altered to account for poor circulation. In other embodiments, a clinician could recognize that a patient may be immune compromised or have other relevant health conditions that may affect wound therapy treatment. The clinician may use these health-related factors to modify the 3D model in any suitable manner. In other embodiments, instead of or in additional to the clinician's contribution to the model, the scanning software can automatically generate a 3D model of the wound by automatically identifying the properties of the various regions of the wound as any of the tissue types or characteristics described herein. Additionally, the 3D model may be modified automatically by a computer algorithm based on the general health characteristics of the patient. Generally, any task described herein this section or throughout the specification as to be performed by a clinician may also be automated to be performed via a computing or generally automated process.

In some embodiments, the characteristics of the wound can be translated into data points that correspond to spatial points within the 3D model. Thus, spatial points of the 3D wound model may have corresponding wound characteristic data. Such wound characteristic data then may be used as a basis to modify the wound model to build in a corresponding wound filler model or to create a separate, independent wound filler model.

As described herein this section and elsewhere in the specification, a 3D wound filler model suitable for 3D printing or other custom means of fabrication can be generated from the 3D model of the wound. However, the 3D model of a wound filler need not be generated from a 3D model of a wound. Instead the 3D model of the wound filler can be designed manually by a clinician with assigned characteristics as needed. The clinician may use their assessment of the wound to identify and define particular regions of the wound filler to correspond with characteristics of the wound. In preferred embodiments, the wound filler is designed to facilitate the application of negative pressure to the wound and/or to irrigate the wound. In certain embodiments, the clinician may consider the long term closure of the wound in designating the characteristics of the wound filler. For example, the clinician may construct the 3D model with the direction of closure in mind, such as by aligning the closure along the Langer lines or along a shorter axis of the wound.

As is described herein this section and elsewhere in the specification, the 3D wound filler model is comprised of various regions that may have variable physical, chemical, and structural characteristics as is desired to treat the wound. The physical, chemical, and structural characteristics of the wound filler model can be determined from the corresponding characteristics of the 3D wound model or via any process as described herein this section or elsewhere in the specification. In some embodiments, the physical, chemical, and structural characteristics of the wound filler model can also be assigned. The different regions may have significant structural differences or utilize different materials as is appropriate for treatment of a wound. The different regions may have various chemical properties as is desired for proper treatment of a wound. In preferred embodiments, the different regions of the wound filler are tailored for the application of negative pressure as is desired for wound healing. In some embodiments, the 3D wound filler model is generated automatically based on characteristics of the wound, while in other embodiments the 3D wound filler information is input manually.

In certain embodiments, a 3D model of the wound filler is created merely from the spatial data contained within the 3D wound model. Such an embodiment may generate a wound filler that accommodates the width, length, and appropriate depth of a wound and could be desirable for the treatment of an irregularly shaped wound as described above. In preferred embodiments, the 3D model of the wound filler is created from multiple different wound characteristics that were incorporated into the 3D model of the wound. The 3D model of the wound filler may also be further determined by the general health-related characteristics of the patient.

As described above, in some embodiments, the characteristics of the various regions of the wound filler may be determined by the anatomical location of the wound and the surrounding tissues. For example, a wound filler used for the treatment of an abdominal wound may comprise a slit structure. In another example, a region of a wound filler associated with a bone or tendon could be constructed from a hydrophilic material with a reasonably closed cell structure so as to maintain moisture in the surrounding tissue. In some embodiments, a fine pore size in the range of about 10-350

μm may be used to maintain moisture. In still another example, the wound filler region in the area of a pressure ulcer or highly exudating tissue may incorporate an open structure such as a reticulated foam so as to better remove liquid from the tissue. In some embodiments, a larger pore size in the range of about 350-900 μm may be used to aid in liquid removal. In some embodiments, any of the pore sizes disclosed in UK Application No. GB1109500.7, titled "WOUND CONTACTING MEMBERS AND METHODS," filed Jun. 7, 2011, and hereby incorporated by reference in its entirety. Open structures may also be used in areas of the wound where granulation tissue is desired.

In certain embodiments, as described above, characteristics of the various regions of the wound filler may be determined automatically based on the 3D wound model or could be assigned. In some embodiments, the characteristics may include water/vapor permeability, gas permeability, absorption capacity, thickness, material type, material structure (such as number of layers), thickness/size, presence of pharmacological additives, color, hydrophobicity/hydrophilicity, or any other suitable characteristic.

The various regions of the wound filler such as determined by the 3D wound model may comprise different materials or have different structural characteristics. In non-limiting embodiments, regions of the wound filler may be comprised of: various rigid, semi-rigid, or soft foams; various hydrophilic and/or hydrophobic foams; soft, conformable, and preferably resiliently flexible materials such as polymers, including thermoplastics; various biodegradable materials; cellulose materials, superabsorbers, or other suitable materials. Suitable polymers include ABS synthetic rubbers, various silicones such as Integra, polyurethanes such as the Elastollan series Thermoplastic polyurethane elastomers (TPUs) from BASF and specifically the Elastollan series hydrophilic TPU, ethylene vinyl acetate, nylons for example Nylon 618 from Taulman 3D Missouri, polyamides, and polyethylenes. The Tangoplus family of resins, e.g. Tangoplus FC930, from Stratsys have varying levels of hardness so that structures with different degrees of flexibility and compression can be fabricated. Further examples of possible materials include 3D knit spacer fabrics such as those manufactured by Gehring Textiles. The wound filler may also include anistropic materials such as the coil-like materials found in U.S. patent Ser. No. 10/981,119, filed Nov. 4, 2011, titled "WOUND PACKING MATERIAL FOR USE WITH SUCTION," issued as U.S. Pat. No. 7,754,937 and hereby incorporated by reference in its entirety and hereinafter referred to as the '937 patent. The potential repeating of individual sections of this material is described in greater detail in the fabrication section below.

As described herein this section and elsewhere in the specification, in some embodiments, the wound filler may have varied structural characteristics such as porosity. In a preferred embodiment, the 3D printer (described further below) may control the porosity of the resulting material, either in the bespoke filler as a whole or by varying the porosity through different sections of the device. For example, a wound filler with smaller pores may be preferable to minimize tissue growth or adhesion, while larger pores may be useful to promote removal of wound exudate from the wound. Such a configuration may thus comprise, for example, a material with smaller pores in contact with the wound which encapsulates or is placed underneath a material with larger pores. Preferably, smaller pores may measure between about 20 to 150 μm, while larger pores may measure between 400-3000 μm or greater. Still other pores may measure less than about 20 μm, less than about 1 μm, or between about 150 to 400 μm. In another example, porosity may be reduced in applications where scar tissue (resulting from excess granulation tissue) should be minimized. In some cases, the number of pores per unit area may be reduced, for example, some embodiments may provide for a wound contacting layer of the bespoke wound filler having an open area of approximately 20%, and 1 mm diameter pore sizes. In certain embodiments, other structural characteristics may be varied within the material, such as to make the material open-celled with interconnected cavities within the material and/or closed-celled. The structural characteristics of the wound filler are limited only by the capabilities of the 3D fabrication device, and thus all manner of structures and shapes suitable for wound treatment may be used.

In some embodiments, the wound filler is tailored for the application of negative pressure. As described above in relation to FIG. 4, and elsewhere in the specification, the wound filler may be designed to have various levels of porosity. In some embodiments, the porosity may be varied to promote liquid flow from portions of the wound via the application of negative pressure. To better control the application of negative pressure, portions of the bespoke wound filler may be made to cover portions of the anatomy from which minimal or no fluid removal is desired. For example, some tissue types, such as exposed bone or tendon, may dry out or be adversely impacted due to the application of negative pressure therapy. Manufacturing a bespoke wound filler that has minimal or no pores when placed over such tissue anatomy may thus be advantageous. Preferably, the bespoke wound filler is manufactured so that other parts of the tissue anatomy in that same wound that would benefit from a porous wound filler (e.g., epithelial tissue) are in contact with a material that has increased porosity.

In addition to altering the porosity of the wound filler to accommodate the desired application of negative pressure, the wound filler may contain flow channels that direct wound exudate drawn via negative pressure. Such flow channels may be oriented horizontally through the wound filler and/or may be oriented vertically. Regions of the filler where limited or no negative pressure is desired may have few if any channels. In certain embodiments, the material characteristics of the wound filler may also be further tailored to accommodate negative pressure such as by using hydrophobic materials like hydrophobic foam to allow for the application of negative pressure without trapping fluid. In some embodiments, hydrophilic materials may be used to trap wound exudate drawn from the surrounding wound tissues. The hydrophilic materials may be superabsorbers. The various regions of the wound filler may be open celled, closed celled, or a combination of the two as is needed to apply desired levels of negative pressure. In some embodiments, particular regions of the wound filler may be constructed as wicking layers to wick fluid in a desirable manner. As described herein this section and elsewhere in the specification, different regions of the wound filler may have different functions and properties, such that the application of negative pressure to various areas of the wound can be well controlled.

In some embodiments, the bulk of the wound filler comprises open-celled hydrophobic material to allow for fluid flow via the application of negative pressure. In certain embodiments, this significant bulk of open-celled hydrophobic material may be surrounded by other materials suited for more direct contact with the wound tissues.

In some embodiments, the 3D wound filler may be tailored for the application of irrigation to the wound. In certain embodiments, the wound filler is connected to one or more reservoirs containing irrigant fluid. Such irrigant fluid may contain antimicrobial molecules, anti-inflammatory molecules, marking molecules, or growth factors that promote wound healing. Irrigant fluid may be applied simultaneously with the application of negative pressure, such that simultaneous irrigation and aspiration is possible. In other embodiments, aspiration then irrigation or irrigation then aspiration are sequential.

The use of irrigation may be desirable for certain regions of the wound, thus the wound filler may be tailored to best apply irrigation to those regions of the wound. For example, in drier areas of the wound or in areas requiring debridement via irrigation, the wound filler may be configured to allow greater irrigant flow to the wound. Such an application may include wound filler regions comprising flow channels, such as those described above in relation to negative pressure, that direct fluid flow towards specific portions of the wound. In other embodiments, regions of the wound filler directed towards irrigant flow may be more porous or be open-celled, thus allowing for greater flow of irrigant fluid. In areas of the wound where irrigation is less desirable, portions of the wound filler may be made to be more occlusive, with smaller or nonexistent pores, or a closed-cell structure.

In some embodiments, the 3D wound filler model may be constructed such that the filler has different layers of material and structure. For example, in a penetrating wound, the filler may have layers of softer material deeper in the wound, with layers of more rigid material closer to the uppermost surface of the wound, thus allowing for the deeper portions of the wound to close before the portions of the wound that are closer to the exterior. In some embodiments, the central portion of the filler may be comprised of one material and/or structure while an exterior portion is comprised of a different material and/or structure. In further embodiments, the wound filler may be layered similar to an onion, with various layers with differing material or structural properties surrounding one another. In further embodiments, the layers may be oriented in a vertical manner such that each layer comprised a flattened section in the horizontal plane.

Figure 5A:
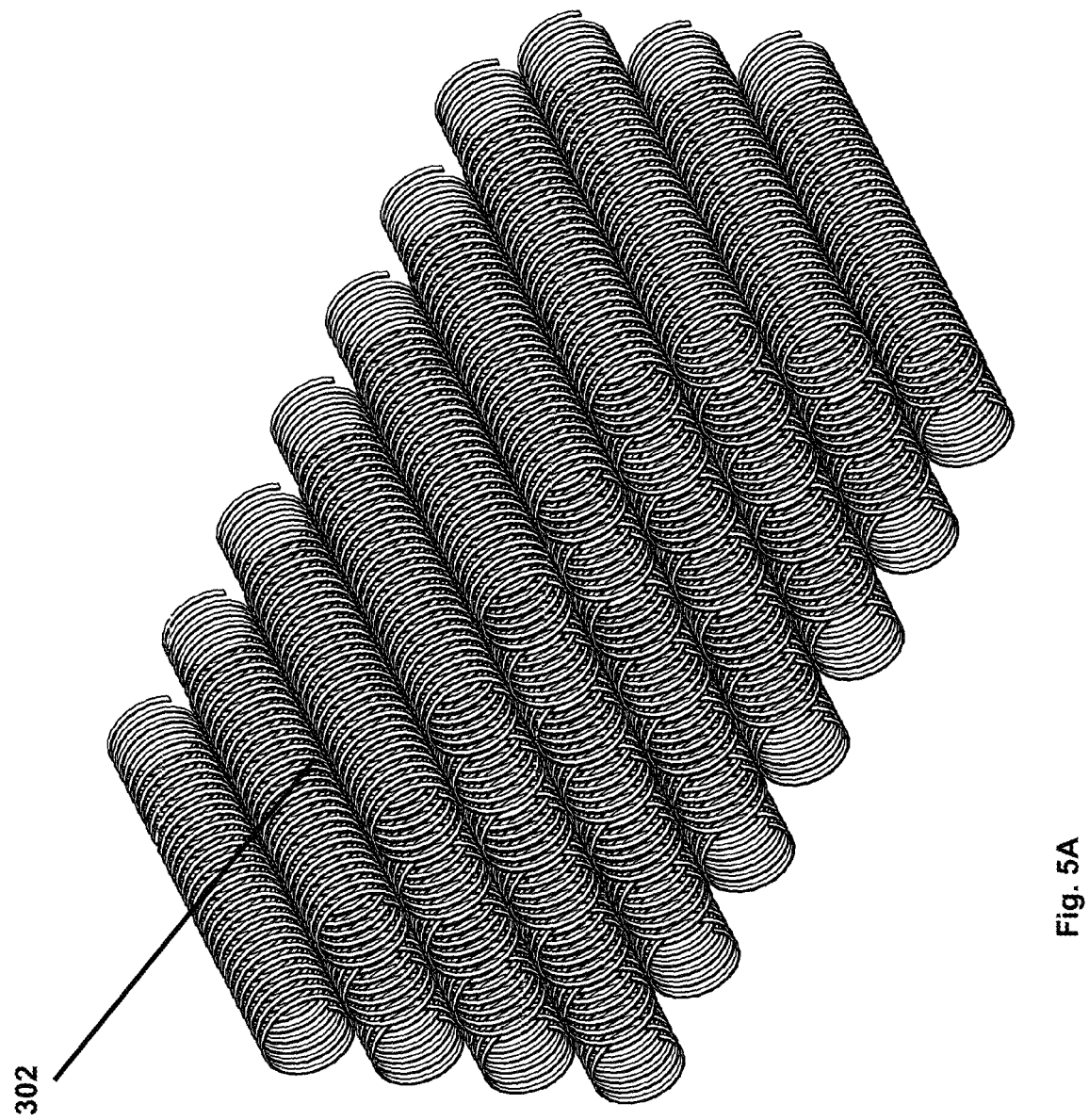
FIGS. 5A-C are photographs of an embodiment of a repeating building block that may be used as a bespoke wound filler system.
Figure 5B:
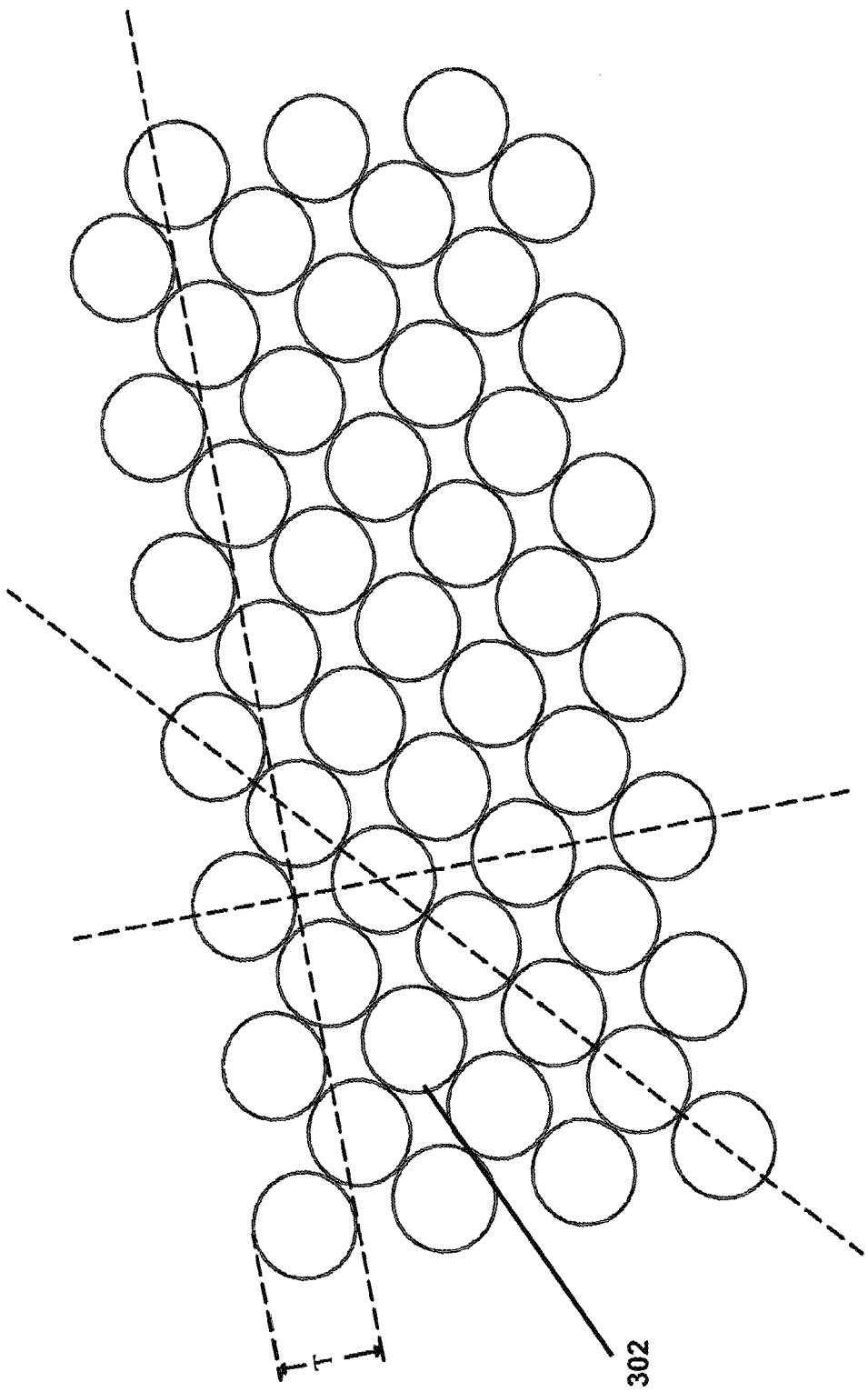
Figure 5C:
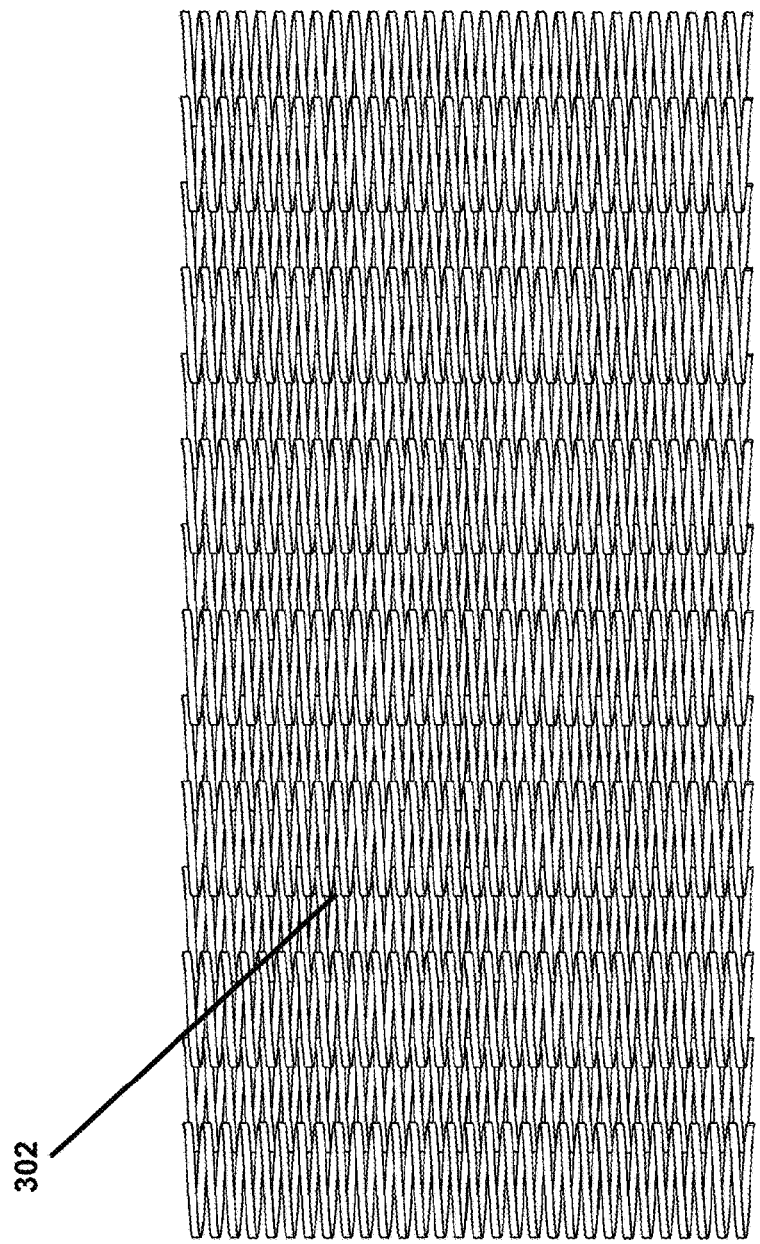

As described above in relation to the design of the wound filler, FIGS. 5A-C illustrate different views of a wound filler 302 which may comprise an anisotropic structure having a first compressive response along a first axis and a second compressive response along a second axis perpendicular to the first axis, the second compressive response being different from the first compressive response. In one embodiment, this structure may be nonabsorbent, and may comprise stacked, coil-like repeating units 302. This and other embodiments of wound fillers may be manufactured by the 3D printer with reference to a 3D model, and examples of such may be found in the '937 patent, incorporated into this application above. The materials described in the '937 patent have anisotropic properties, meaning that their material properties may be dimensionally dependent. For example, as described above, an anisotropic material may have increased stiffness in one direction versus another direction. Thus, a material with anisotropic properties such as those depicted in the '937 patent may collapse more readily in one direction rather than another. Such a material could be used within the wound to control the compression of the wound filler in particular directions and preferentially compress the filler to allow for improved wound closure. The material of the '937 patent is nonabsorbent, thus this material may allow for the passage of negative pressure. In some embodiments, the material of '937 may further be used in combination with negative pressure strategies to direct the application of negative pressure and wound closure, in a manner consistent with the embodiments described herein this section and elsewhere in this specification.

The materials that comprise the wound filler may be determined by the characteristics of a particular region of the 3D wound model or may be assigned. For example, an area of the wound that requires additional hydration could utilize a moist hydrophilic material such as a hydrogel. An area that is highly exudating may need to be highly absorbing and have a high water vapor evaporation. Areas with low levels of wound exudate may require a nonabsorptive material with low water vapor permeability so as to trap moisture.

Since a 3D printer is capable of printing a wide variety of shapes, in some embodiments, the 3D model may also include a port and/or tubing such that the wound filler may be connected to a source of negative pressure. In further embodiments, the 3D model includes additional suitable articles that may be useful for wound healing.

In some embodiments, the material may be configured as a scaffold material to promote tissue ingrowth and/or bioabsorption. For example, bioabsorption can be achieved by using polyglycolic or polylactic acids or co-polymers of these polymers, for the printing of the scaffold, and which then may be seeded with cells and/or cell growth promoters. Antibiotics, anti-inflammatory drugs, diagnostic agents such as radioopaque markers, and other such materials may also be incorporated therein. The scaffold material may be tailored to deliver a variety of molecules in the form of controlled delivery. For example, one region of the filler could deliver an antimicrobial molecule to an infected region of tissue, while another region of the filler delivers an anti-inflammatory molecule to an inflamed region of tissue. Various molecules may be released in to the surrounding tissue as is merited by the characteristics of the surrounding tissue. Released molecules are not limited only to locally acting molecules, in some embodiments systemically acting drugs may be released.

The wound filler is not limited to one continuous, intact structure. The wound filler can be constructed to be in separate pieces and applied separately to the wound rather than as a single unit. It should be understood that all embodiments described herein this section or elsewhere in the specification may be generated as a single continuous structure or as separate dividable portions. This approach is particularly useful for dealing with undetermined structures of wounds or tunneling wounds where it may not be possible to insert a single wound filler In some embodiments, the wound filler may be constructed as a rounded bowl-like shape, or may comprise a rounded bowl-like shape at the bottom of the filler. This bowl-like shape can be a comprised of a single material layer such as a foam bowl. In certain embodiments, the bowl comprises one material while a remainder of the wound filler positioned above or within the bowl comprises a different material. In some embodiments the bowl portion of the filler may be in the form of a divided separate section of the wound filler.

Fabrication of the 3D Wound Filler

Having generated the 3D model, the 3D model can be used by a 3D printing device to manufacture the bespoke wound filler. The 3D printing device may be any suitable 3D printer, including by means of example only the Objet Connex500™, the 3D Systems ZPrinter® 850, or the RepRap. In other embodiments, wound filler fabrication may be performed using any known wound dressing fabrication technique. The wound filler may be fabricated from any materials described herein this section or elsewhere within the specification, or any other type of suitable material. The wound filler may be fabricated to comprise any structure described herein this section or elsewhere within the specification, or any structure that may be suitable for the wound filler. The wound filler may be fabricated to comprise any characteristic described herein this section or elsewhere within the specification, or any characteristic that may be suitable for the wound filler.

In some embodiments, the wound filler may be fabricated separately from the wound and later placed within the wound. In other embodiments, the wound filler may be created directly in the wound. In still other embodiments, a portion or portions of the wound filler may be created separately from the wound, while a portion or portions of the wound filler may be created directly in the wound.

As described above, the wound filler may be fabricated via any known fabrication technique. In some embodiments, the wound filler may be fabricated via extrusion or via electrospinning techniques. The wound filler can also be fabricated via gas blowing or localized deposition directly into the wound or onto a substrate.

In some embodiments, the outermost or topmost layer of the wound filler can be comprised of a fluid impermeable polymer, such as silicone. This outermost or topmost layer can overlay the top of the wound filler and extend beyond the edges of the wound. This outermost or topmost layer can further comprise an adhesive or other means for sealing the outermost layer around the wound. In this manner, the outermost layer may function as a drape to contain the application of negative pressure. In some embodiments this outermost or topmost layer may be fabricated in combination with a biodegradable wound filler such that once the wound filler biodegrades, the outermost layer is still intact. Similar to the above description of the materials utilized in the design of the wound filler, the 3D printer is configured to manufacture a bespoke filler from soft, conformable, and preferably resiliently flexible materials such as polymers, including thermoplastics. Suitable polymers include ABS synthetic rubbers, polyurethanes for example Elastollan SP9109 from BASF, nylons for example Nylon 618 from Taulman3D Missouri, polyamides, ethylenevinyle acetates, and polyethylenes. The Tangoplus family of resins, e.g. Tangoplus FC930, from Stratsys have varying levels of hardness so that structures with different degrees of flexibility and compression can be fabricated. In further embodiments, the materials utilized to construct the wound filler and other components of the wound treatment system encompass all materials disclosed in this section and elsewhere in the specification.

As described above in relation to the design of the wound filler, in some embodiments, the 3D printer may be capable of depositing materials or using materials that form a porous configuration. In some embodiments, the materials may be harder, and may include porous scaffolding materials such as hydroxyapatite that promote tissue growth. The 3D printer may be configured to use multiple materials so as to form a bespoke wound filler composed of multiple devices. In some embodiments, the 3D printer is capable of manufacturing a bespoke wound filler consisting of a repeating building block, for example the building blocks described herein this section and elsewhere in the specification.

Some embodiments may also provide for regions of the wound filler to be constructed from repeating building blocks. The use of repeating building blocks may be advantageous during manufacture because these building blocks could be replicated over and over again within the model allowing for an easier and more efficient creation of structures within the filler. Further, the use of building blocks may allow for the 3D fabrication device and/or the associated software to operate more efficiently. For example, the use of building blocks may allow the fabrication device to move through tight, specified patterns and limit the required movement and energy consumption of the device. In some embodiments, the repeating unit may be comprised of any physical, chemical, or structural characteristics as described herein this section or elsewhere in the specification. Different regions of the wound filler may be comprised of different building blocks, allowing for a complex construction of layered and/or stacked building blocks of different types. For example, one region comprising a repeating building block may utilize building blocks of foam having a desired porosity, structure or other characteristics. A second region may comprise repeating building blocks made from a different material such as the coil-like material described in '937 patent and depicted as 302 in FIGS. 5A-C. Based on the 3D model, repeating blocks may have different characteristics for positioning in different parts of the wound. The software for the 3D printer or other fabrication device may set the contours of the 3D model as the limits for a repeating building block and repeat the building block in three dimensions until it reaches the limit of a contour.

Preferably, for small details, the 3D printer can manufacture details in a range of at least about: 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm or 100 µm. Details between 30-50 µm may be conducive to obtaining good tissue growth. In some embodiments, the 3D printer is configured to manufacture bespoke wound fillers as detailed in PCT Application PCT/GB2012/000489, filed Jun. 7, 2012, titled "WOUND CONTACTING MEMBERS AND METHODS, APPARATUSES, SYSTEMS AND KITS INCORPORATING THE SAME," published as WO20122168678 and which is hereby incorporated by reference in its entirety.

Applying the Bespoke Wound Filler

As is described herein this section and elsewhere in the specification, the bespoke wound filler may be applied to a wound in combination with other conventional wound healing related articles, such as a drape, vacuum source, foam, tubing, reservoir, bandage, adhesive, or any other articles suitable for the treatment of wound. In certain embodiments the bespoke wound filler may be combined with other wound fillers, such as a bowl-shaped foam that may be placed underneath the wound filler as described above. In some embodiments, these other wound healing articles may be constructed alongside the wound filler via suitable 3D fabrication equipment. In certain embodiments, these other wound care articles or components may be fabricated as attached to the bespoke wound filler to form a wound treatment apparatus.

Figure 6A:
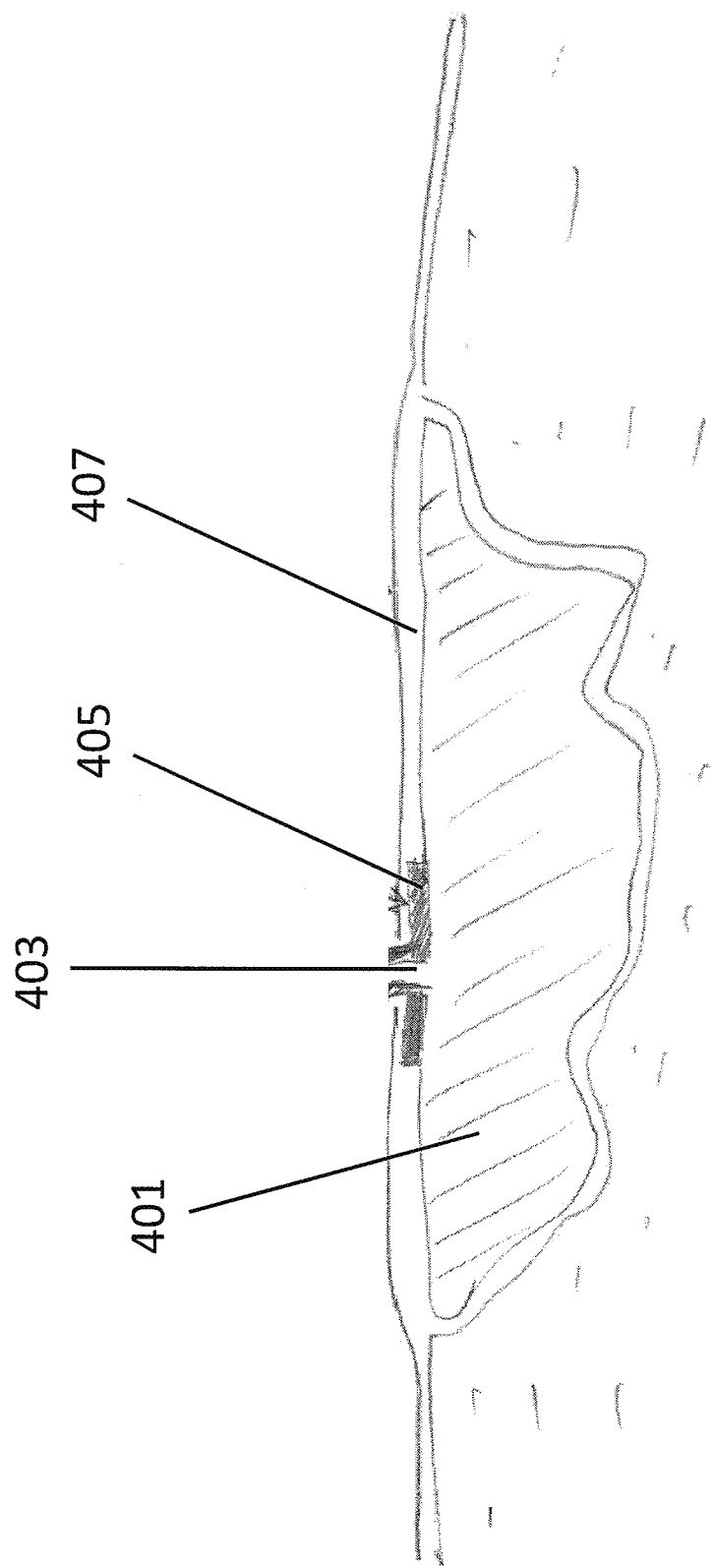
FIGS. 6A-B are schematic illustrations of embodiments of a wound treatment apparatus comprising a bespoke wound filler.
Figure 6B:
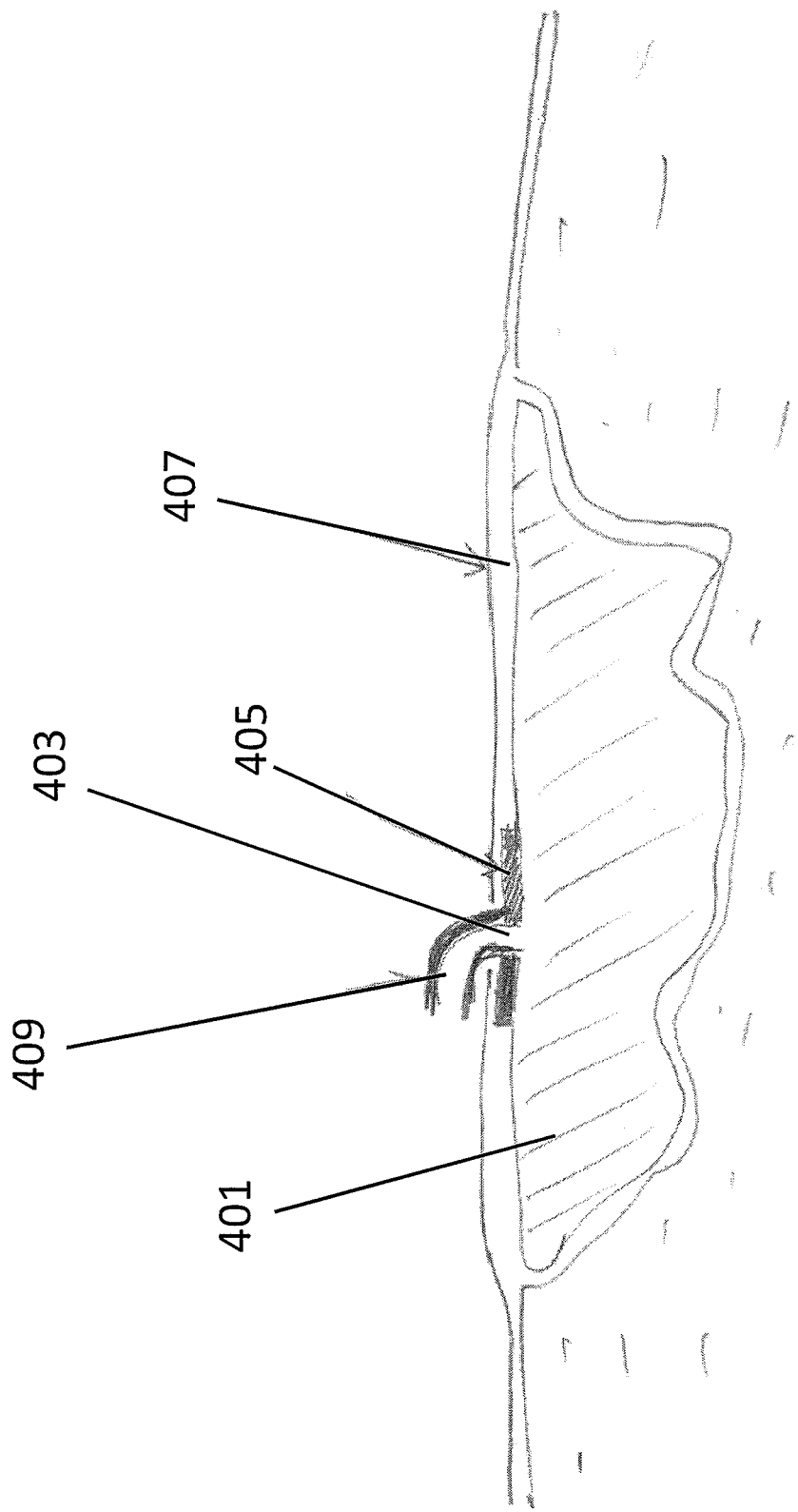

FIGS. 6A-B illustrate different views of a wound treatment apparatus comprising a wound filler, similar to the wound treatment apparatuses and wound fillers described herein this section and elsewhere in the specification. FIG. 6A illustrates a wound treatment apparatus comprising a bespoke wound filler 401 as described herein this section and elsewhere in the specification. The wound treatment apparatus further comprises an opening 403, which may be connected to a source of negative pressure such as a suitable pump or other related structures such as a port or filter. One example of a suitable pump is the Renasys EZ pump available from Smith & Nephew. The apparatus may further comprise a flat sealed surface 405 that allows for sealing of the drape 407. In some embodiments, the flat sealed surface immediately surrounds the opening 403, such that the drape 407 can seal around the opening 403. In certain embodiments, the flat sealed surface could be extended to the wound edge or beyond and sealing strips applied as is described in the PICO system available from Smith & Nephew. In some embodiments, the drape 407 may extend beyond the edges of the wound and may be sealed to the edges of the wound via any suitable means such as via an adhesive, or via sealing strips such as those disclosed above.

Similar to the apparatus described in FIG. 6A and elsewhere in the specification, FIG. 6B illustrates a wound treatment apparatus comprising a bespoke wound filler 401 as described herein this section and elsewhere in the specification. The wound treatment apparatus further comprises an opening 403, which may be connected to a source of negative pressure such as a suitable pump. The apparatus may further comprise a flat sealed surface 405 that allows for sealing of the drape 407. The apparatus also comprises an integral port 409 to allow for ease of connection to a source of negative pressure. The port, as with all of the components described in relation to FIGS. 6A-B, may be fabricated directly via 3D fabrication techniques. In some embodiments, the bespoke wound filler 401 is fabricated directly attached to the port 409.

In certain embodiments, to aid the clinician in the proper orientation of the bespoke wound filler, marks may be printed on the wound filler or dermis surface such that it allows the clinician to properly orient and place the filler within the wound. These marks may be arrows, lines, words, or any other marking that will aid in placement of the filler. In certain embodiments, anatomical terms or general terms may be used to mark the filler, for example, words such as "foot," "head," or "distal" may be used to direct the clinician in any desirable manner. In certain embodiments, marks are also made on the tissue surrounding the wound to allow for ease of orientation of the filler and wound treatment system In some embodiments, the bespoke wound filler may be replaced multiple times over the course of closure of a wound. The wound filler can be replaced with another fabricated wound filler that may be better suited to the wound at this later stage in the healing process. For example, a wound filler inserted earlier in the healing process may comprise bioactive molecules that are primarily directed towards the early inflammatory stages of the host response to a wound while a later wound filler may comprise bioactive molecules that are better suited to latter stage tissue repair. In other embodiments, wound fillers of various shapes may be used at different stages of the wound healing process. For example, a larger wound filler could be used earlier in the healing process before much closure of the wound has occurred. At a later time, once the wound has closed to some degree, a smaller wound filler may be used as it may be better suited to the wound. The wound filler could be replaced after at least about: 1 hour, 3 hours, 6 hours, 12 hours, 24 hours, 2 days, 4 days, 7 days, 14 days, 21 days, 28 days, or more than 28 days.

In some embodiments, the methods and apparatuses described above can be applied to create a 3D model for a wound dressing that need not fill a wound, but may be placed over a wound (such as with an incisional wound). For example, a 3D model for an entire or portion of a wound dressing may be constructed having multiple layers, each with discrete properties, such as described with respect to the multiple applications incorporated above regarding wound treatment apparatuses and methods incorporating absorbent materials. The layers may be customized by the model to optimize certain properties, such as absorbency, fluid transfer, etc., based on the type, size and characteristics of the wound being treated and the treatment modality (e.g., negative pressure wound therapy). The 3D printing methods or other techniques as described above may then be used to fabricate the wound dressing.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A method of manufacturing a bespoke tissue treatment apparatus for use in treating a damaged region of tissue, the method comprising:
   scanning a tissue location to obtain a three-dimensional model of an area to be treated;
   modifying the three-dimensional model of the area to be treated to generate a three-dimensional model of a bespoke tissue treatment apparatus using a repeating building block, wherein said modifying accounts for attributes of the tissue location and for a treatment modality; and
   fabricating a bespoke tissue treatment apparatus based on the generated three-dimensional model of a bespoke tissue treatment apparatus.

2. The method of claim 1, wherein the three-dimensional model of an area to be treated is obtained using a device selected from the group consisting of laser scanners, stereo-optical scanners, and cameras with depth sensors.

3. The method of claim 1, wherein the area to be treated comprises bone.

4. The method of claim 1, wherein the area to be treated comprises a ligament.

5. The method of claim 1, wherein the three-dimensional model of a bespoke tissue treatment apparatus comprises repeating blocks having different characteristics for positioning in different parts of the area to be treated.

6. The method of claim 1, wherein modifying the three-dimensional model of an area to be treated accounts for one or more tissue types present in the area to be treated.

7. The method of claim 1, wherein the bespoke tissue treatment apparatus is fabricated with a three-dimensional printer.

8. The method of claim 1, wherein modifying the three-dimensional model of an area to be treated comprises determining a suitable porosity for the bespoke tissue treatment apparatus.

9. The method of claim 1, wherein the three-dimensional model of the bespoke tissue treatment apparatus has variable porosity.

10. The method of claim 1, wherein fabricating the bespoke tissue treatment apparatus comprises fabricating a first portion of the bespoke tissue treatment apparatus using a first porosity, and fabricating a second portion of the bespoke tissue treatment apparatus using a second porosity, the first porosity being smaller than the second porosity.

11. The method of claim 1, wherein the bespoke tissue treatment apparatus is fabricated from a polymer.

12. The method of claim 1, wherein the bespoke tissue treatment apparatus is fabricated from a porous scaffolding material.

13. The method of claim 1, further comprising seeding the bespoke tissue treatment apparatus with one or more of cells or cell growth promoters.

14. The method of claim 1, wherein the bespoke tissue treatment apparatus is fabricated from two or more different materials.

15. The method of claim 10, wherein the first porosity comprises pores measuring between about 20 to 150 μm and the second porosity comprises pores measuring between about 400-3000 μm.

* * * * *